United States Patent
Schimperna et al.

(10) Patent No.: US 9,290,483 B2
(45) Date of Patent: Mar. 22, 2016

(54) AROMATIC MONOMERS DERIVING FROM GLYCEROL UNITS, PROCESS FOR THEIR PREPARATION AND USE THEREOF FOR THE PREPARATION OF WATER-SOLUBLE CONJUGATED POLYMERS

(75) Inventors: Giuliana Schimperna, Novara (IT); Riccardo Po', Novara (IT); Andrea Pellegrino, Trecate (IT); Maria Caldararo, Trecate (IT)

(73) Assignee: ENI S.p.A., Rome (IT)

( * ) Notice: Subject to any disclaimer, the term of this patent is extended or adjusted under 35 U.S.C. 154(b) by 285 days.

(21) Appl. No.: 13/643,438

(22) PCT Filed: Apr. 29, 2011

(86) PCT No.: PCT/IB2011/000941
§ 371 (c)(1),
(2), (4) Date: Oct. 25, 2012

(87) PCT Pub. No.: WO2011/138655
PCT Pub. Date: Nov. 10, 2011

(65) Prior Publication Data
US 2013/0046072 A1    Feb. 21, 2013

(30) Foreign Application Priority Data
May 3, 2010 (IT) .................................. MI10A0769

(51) Int. Cl.
| | |
|---|---|
| C08G 65/26 | (2006.01) |
| C08G 65/04 | (2006.01) |
| C07D 317/22 | (2006.01) |
| C07D 409/12 | (2006.01) |
| C07D 405/12 | (2006.01) |
| C08G 61/12 | (2006.01) |
| H01L 51/00 | (2006.01) |
| H01L 51/42 | (2006.01) |

(52) U.S. Cl.
CPC ............ C07D 405/12 (2013.01); C07D 317/22 (2013.01); C07D 409/12 (2013.01); C08G 61/123 (2013.01); C08G 61/124 (2013.01); C08G 61/126 (2013.01); C08G 2261/124 (2013.01); C08G 2261/1422 (2013.01); C08G 2261/1424 (2013.01); C08G 2261/3142 (2013.01); C08G 2261/3223 (2013.01); C08G 2261/3241 (2013.01); C08G 2261/3246 (2013.01); C08G 2261/411 (2013.01); C08G 2261/91 (2013.01); H01L 51/0036 (2013.01); H01L 51/0039 (2013.01); H01L 51/0043 (2013.01); H01L 51/0068 (2013.01); H01L 51/0072 (2013.01); H01L 51/42 (2013.01)

(58) Field of Classification Search
CPC ....................................................... C08G 65/26
USPC ...................... 528/405; 549/448, 60; 548/444
See application file for complete search history.

(56) References Cited

U.S. PATENT DOCUMENTS

2005/0070710 A1    3/2005    O'Dell et al.

FOREIGN PATENT DOCUMENTS

| GB | 1 427 918 | 3/1976 |
|---|---|---|
| WO | 03 035714 | 5/2003 |

OTHER PUBLICATIONS

Higgins et al; Model coordination—turnable reactivities; American chemical Society; 1998; Chem Abstract 129: 28295.*
Higgins, T., et al., "Model Coordination Complexes for Designing Poly(terthiophene)/Rh(I) Hybrid Materials with Electrochemically Tunable Reactivities," Chemistry of Materials, vol. 10, No. 6, pp. 1589 to 1595, (Jun. 1, 1998) XP 55003274.
International Search Report Issued Aug. 1, 2011 in PCT/IB11/000941 Filed Apr. 29, 2011.

* cited by examiner

*Primary Examiner* — Duc Truong
(74) *Attorney, Agent, or Firm* — Oblon, McClelland, Maier & Neustsdt, L.L.P.

(57) ABSTRACT

Monomers having formula (I) and process for their synthesis which comprises the etherification reaction of a halogen-derivative (Z=Cl, Br, I) having formula (III) with the hydroxyl group of the glycerol derivative (IV), according to the following scheme:(Formula III, IV & I) (III) (IV) (I)

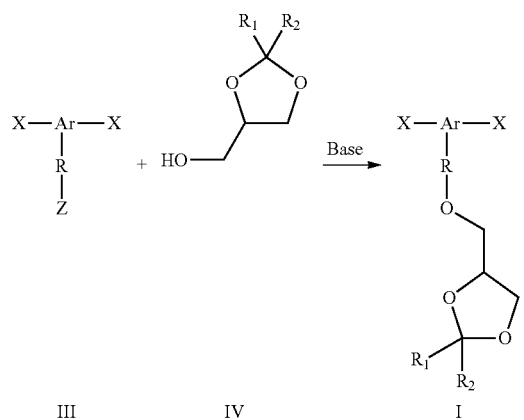

11 Claims, No Drawings

AROMATIC MONOMERS DERIVING FROM GLYCEROL UNITS, PROCESS FOR THEIR PREPARATION AND USE THEREOF FOR THE PREPARATION OF WATER-SOLUBLE CONJUGATED POLYMERS

The present invention relates to aromatic monomers deriving from glycerol units and the process for their preparation as well as their use for the preparation of conjugated polymers/copolymers soluble in water or aqueous mixtures.

As is known, photovoltaic devices are devices capable of converting the energy of a light radiation into electric energy. At present, most photovoltaic devices which can be used for practical applications exploit the physico-chemical properties of photoactive materials of the inorganic type, in particular high-purity crystalline silicon. As a result of the high production costs of silicon, scientific research, however, has long been orienting its efforts towards the development of alternative organic materials having a conjugated, oligomeric or polymeric structure. Unlike high-purity crystalline silicon, in fact, conjugated organic materials are characterized by a relative synthesis facility, the possibility of modulating the physico-chemical properties, a low production cost, a reduced weight of the relative photovoltaic device, in addition to allowing the recycling of said polymer at the end of the life-cycle of the device in which it is used.

The functioning of organic and polymer photovoltaic cells is based on the combined use of an electron acceptor compound and an electron donor compound. In the state of the art, the most widely-used electron donor and acceptor compounds in the devices indicated in scientific and patent literature are n-conjugated copolymers, especially those belonging to the groups of polyparaphenylene vinylenes and polythiophenes, and derivatives of fullerene, respectively.

The basic conversion process of light into electric current in a polymer photovoltaic cell takes place through the following steps:
1. absorption of a photon on the part of the donor compound with the formation of an exciton, i.e. a pair of "electron-hole" charge transporters;
2. diffusion of the exciton in a region of the donor compound in which its dissociation can take place;
3. dissociation of the exciton in the two charge transporters (electron (−) and hole (+)) separated;
4. transporting of the charges thus formed to the cathode (electron, through the acceptor compound) and anode (electronic hole, through the donor compound), with the generation of an electric current in the circuit of the device.

The photo-absorption process with the formation of the exciton and subsequent yielding of the electron to the acceptor compound leads to the transfer of an electron from the HOMO (Highest Occupied Molecular Orbital) to the LUMO (Lowest Unoccupied Molecular Orbital) of the donor and subsequently the passage from this to the LUMO of the acceptor.

As the efficiency of an organic or polymer photovoltaic cell depends on the number of free electrons which are generated by dissociation of the excitons, one of the structural characteristics of donor compounds which mostly influences said efficiency is the difference in energy existing between the HOMO and LUMO orbitals of the donor compound (so-called band-gap). The wave-length of the photons which the donor compound is capable of collecting and effectively converting into electric energy (so-called "photon harvesting" or "light harvesting" process) depends, in particular, on this difference.

The efficiency of a cell is also proportional to the voltage obtainable in the device. It has been demonstrated that the voltage is correlated to the energy difference between the HOMO of the donor and LUMO of the acceptor compound. It is therefore evident that also in this case the energy levels of the materials selected have a fundamental importance.

Another important characteristic is the mobility of the electrons in the acceptor compound and electronic gaps in the donor compound, which determines the facility with which the electric charges, once photogenerated, reach the electrodes. This, in addition to being an intrinsic property of the molecules, is also greatly influenced by the morphology of the photoactive layer which, in turn, depends on the reciprocal miscibility of the components and on their solubility. Finally, a further fundamental characteristic is the resistance to thermo-oxidative and photo-oxidative degradation of the materials, which must be stable under the operating conditions of the device.

In order to obtain acceptable electric currents, the band-gap between HOMO and LUMO must not be excessively high but at the same time it must not be excessively low, as an excessively low gap would jeopardize the voltage obtainable at the electrodes of the device.

In the simplest way of operating, the cells are produced by introducing a thin layer (about 100 nanometres) of a mixture of the acceptor compound and donor compound between two electrodes. In order to produce a layer of this type, a solution of the two components is prepared. A photoactive film is subsequently created on the first electrode starting from the solution, resorting to suitable deposition techniques such as "spin-coating", "spray-coating" "ink-jet printing" and similar. The counter-electrode is finally deposited on the dried film.

Donor materials consist of conjugated aromatic polymers. One of those which is most commonly used in the construction of polymer solar cells is regioregular poly(3-hexylthiophene). This polymer has suitable electronic and optical characteristics (HOMO and LUMO orbital values; absorption coefficient), a good solubility in the organic solvents used for the construction of the cells and a reasonable mobility of the electronic gaps.

Current technologies for the production of polymer cells resort to depositions techniques of thin photoactive layers from solution, coupled with high vacuum processes for the production of the electrodes (or of the same photoactive layer, in case of cells based on low-molecular-weight organic molecules). The deposition from polymer solution resorts to drop casting, spin coating, dip coating spray coating, ink-jet printing, screen printing, roll-to-roll deposition processes etc., and the use of a suitable solvent. The donor polymers are normally dissolved in organic solvents such as toluene, xylene, chloroform, chlorobenzene etc. to guarantee complete solubility. These solvents however are extremely toxic and it is therefore desirable to eliminate them in industrial processes. It would be extremely beneficial to use polymers soluble in aqueous, alcohol solvents or also in hydro-alcohol mixtures or water/acetone, water/dioxane, water/tetrahydrofuran mixtures etc. In this way, in addition to the toxicity, hazards deriving from the potential occurrence of explosions due to the formation of explosive mixtures between air and vapours of organic solvent or drops of finely divided organic solvent, would be significantly reduced.

Due to the chemical structure of the polymers used, however, the solubility of these in water or aqueous mixtures, is practically null.

The Applicant has now found a new group of functionalized aromatic monomers which can generate conjugated polymers/copolymers which are soluble in water or aqueous mixtures.

An object of the present invention therefore relates to monomers having the following general structure (I):

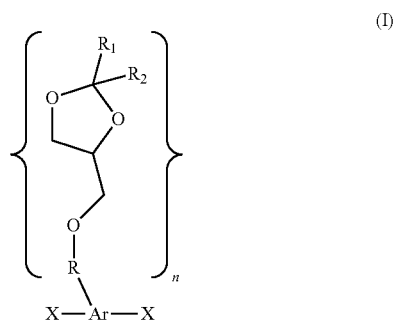

(I)

wherein

Ar is a $C_6$-$C_{12}$ aromatic radical, a $C_{12}$-$C_{18}$ polycyclic aromatic radical, or Ar is a heteroaromatic radical containing one or more heteroatoms such as S, N, Se, O, optionally polycondensed, X is a group which can be polymerized by means of a reaction selected from Suzuki, Stille, Heck or Yamamoto reactions, selected from —Br, —Cl, —I, —O—(SO$_2$)—CF$_3$, —B(OH)$_2$, —B(OR')$_2$, —SnR'$_3$, —B(OR"O) and vinyl, with R' a $C_1$-$C_6$ alkyl radical and R" an ethylene radical, optionally substituted with $C_1$-$C_2$ alkyl groups;

$R_1$ and $R_2$, equal or different from each other, can be a hydrogen atom or a $C_1$-$C_6$ alkyl radical;

R is a divalent $C_1$-$C_{12}$, preferably $C_1$-$C_6$, alkylene radical;

n ranges from 1 to 4, and is preferably 1 or 2.

Preferred monomers according to the present invention are those wherein Ar is a radical deriving from benzene, fluorene, thiophene, carbazole, dithienocyclopentadiene or phenothiazine.

Monomers having the following general formula (II) represent a further object of the present invention:

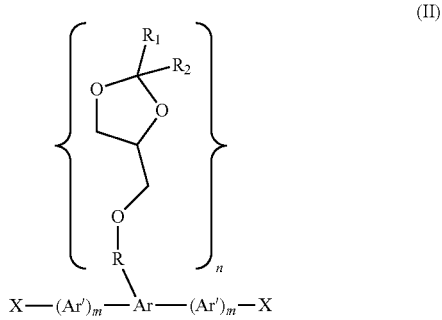

(II)

wherein R, $R_1$, $R_2$, Ar, X, n have the same meanings as indicated above; and Ar' represents a heteroaromatic radical containing a heteroatom such as S, N, Se;

m=1 or 2, m is preferably 1.

Preferred monomers according to the invention are those wherein Ar' is a radical deriving from thiophene, thienothiophene, thiazole, carbazole, dithienocyclopentadiene or phenothiazine.

Monomers having general formula (I) and (II) can be prepared by traditional chemical synthesis techniques. The synthesis of (I), for example, takes place through the etherification reaction (Williamson reaction) of a halogen derivative (Z═Cl, Br, I, preferably bromine) having formula (III) with the hydroxyl group of the glycerol derivative (IV), according to the following scheme 1:

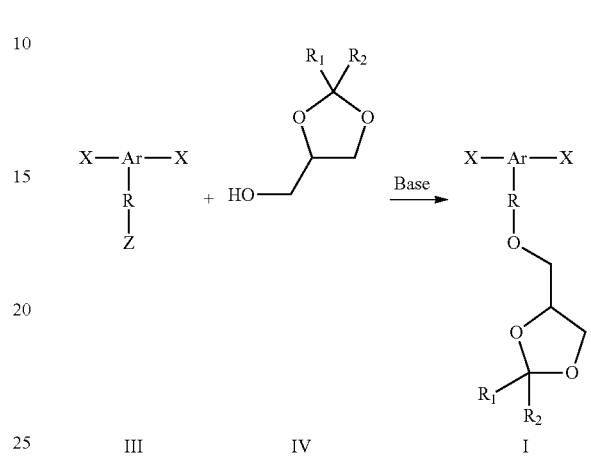

III      IV      I

This type of reaction is known in literature, it is described, for example, in the U.S. Pat. No. 3,960,902. These reactions normally take place in the presence of bases, such as alcoholates, (methylate, ethylate, butylate, terbutylate) of alkaline metals (sodium, potassium, caesium, preferably potassium terbutylate). The reaction is carried out in organic solvents, selected from ethers (for example tetrahydrofuran, dimethoxyethane, etc.), hydrocarbons (benzene, toluene, xylene, etc.), dipolar aprotic solvents (N-dimethylformamide, N-methylpyrrolidone, etc.). The molar ratios III:IV:base used range from 1:1.1:1.15 to 1:3:3.3. The reaction is carried out at temperatures ranging from 15° C. to 150° C., preferably from 20° C. to 80° C. These reactions can also be carried out under phase transfer conditions.

The halogen derivative (III) is synthesized by means of normal organic synthesis techniques, for example alkylation with dihalogen derivatives (VI) (Z═Cl, Br, I) of aromatic systems (V) containing acid hydrogen (easily removable by base treatment), according to the following scheme 2:

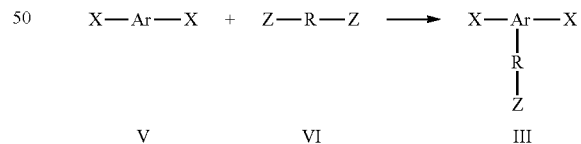

V      VI      III

The synthesis of halogen derivatives (III) is known in the art, some examples present in literature are: Macromol. Rapid Commun. 2008, 29, 390; JACS 2003, 125, 6705; Synthetic Metals 2007, 157, 813; Journal Polymer Science: Part A: Polymer Chemistry 2008, 46, 4407.

The glycerol derivative (IV) can be prepared using normal synthetic technologies, by the acid catalyzed reaction of glycerine (VII) with a derivative containing a carbonyl functionality (VIII), $R_1$ and $R_2$ have the meanings previously defined in general formula (I). The reaction is described by scheme 3:

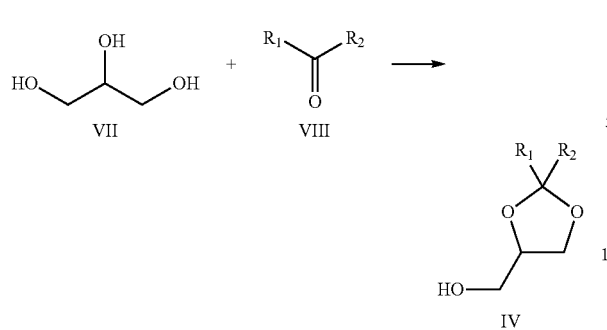

The synthesis of these compounds is known in the art, this reaction is widely described in Synthesis 1981, 501.

The compounds having general formula (II) are prepared starting from the compounds having general formula (I) by means of a metal-assisted condensation reaction and subsequent halogenation of the derivative obtained. The compounds having general formula (I) react with aromatic compounds having general formula (IX) (W=—SnR'$_3$, —B(OH)$_2$, —B(OR)$_2$), to give condensation products having formula X as described in the following scheme 4:

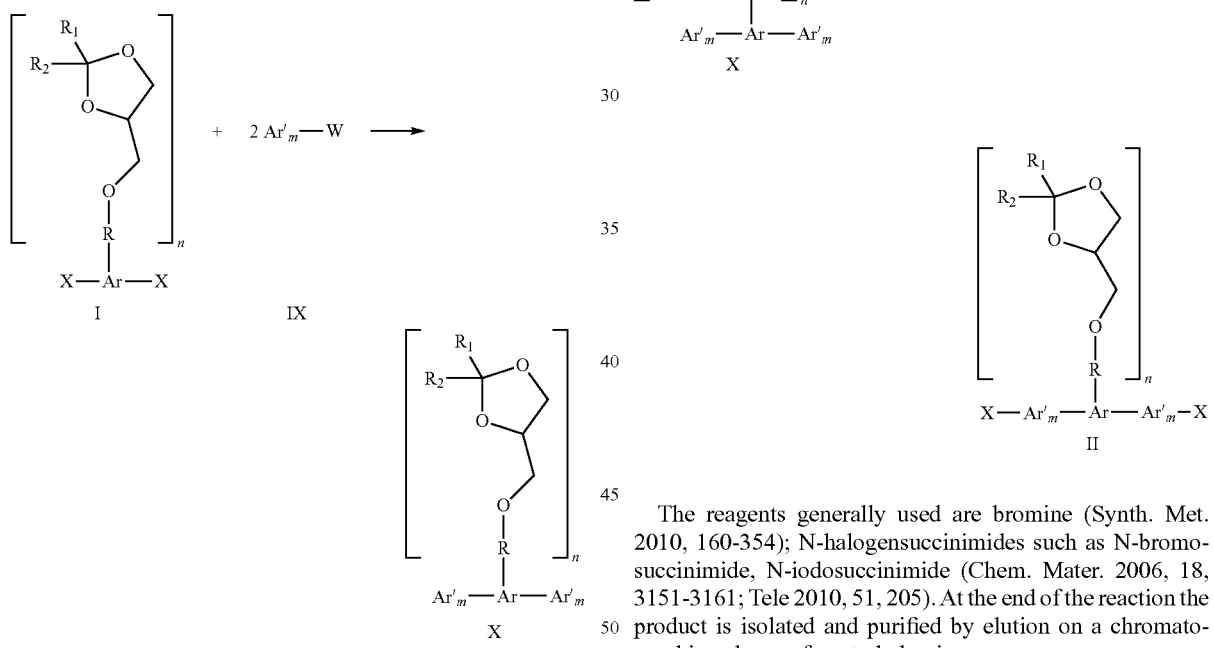

In literature there are various examples of these condensation reactions (Chem. Mater. 2006, 18, 3151-3161; Chem. Eur. Journal 2009, 15, 4906). The Suzuki reactions (W=— B(OH)$_2$, —B(OR)$_2$) and Stille reactions (W=—SnR'$_3$) are catalyzed by palladium complexes, such as Pd(PPh$_3$)$_4$, PdCl$_2$(PPh$_3$)$_2$, the catalysts can also be prepared in situ, starting from PdCl$_2$ or Pd(OAc)$_2$ and the suitable phosphine (for example, triphenylphosphine (PPh$_3$, tris-ortho-tolylphosphine, tris-paratolylphosphine). The molar ratios (I):(IX) between the reagents range from 1:2 to 1:4. The catalyst is used with molar ratios (I):cat. ranging from 1: 0.008 to 1:0.02.

The reaction can be carried out in ether solvents (for example dimethoxyethane, tetrahydrofuran), dipolar aprotic solvents (for example N,N-dimethylformamide, N-methylpyrrolidone) or hydrocarbon solvents such as toluene, xylene, etc. In the case of the Suzuki reaction, when W=—B(OH)$_2$, —B(OR)$_2$, the presence of a base is necessary (for example, sodium or potassium bicarbonate, sodium or potassium carbonate) used in molar ratios I:base ranging from 1:1 to 1:20. The base is generally dissolved in degassed water. The aqueous solution can have a concentration ranging from 1M to 3M, preferably 2M. The reaction is carried out at temperatures ranging from 10 to 200° C., preferably from 30 to 150° C. At the end of the reaction, the condensation product (X) is isolated and purified by elution on a chromatographic column of neutral alumina.

The product X thus obtained is subsequently halogenated by normal halogenation techniques of aromatic systems, as described in scheme 5:

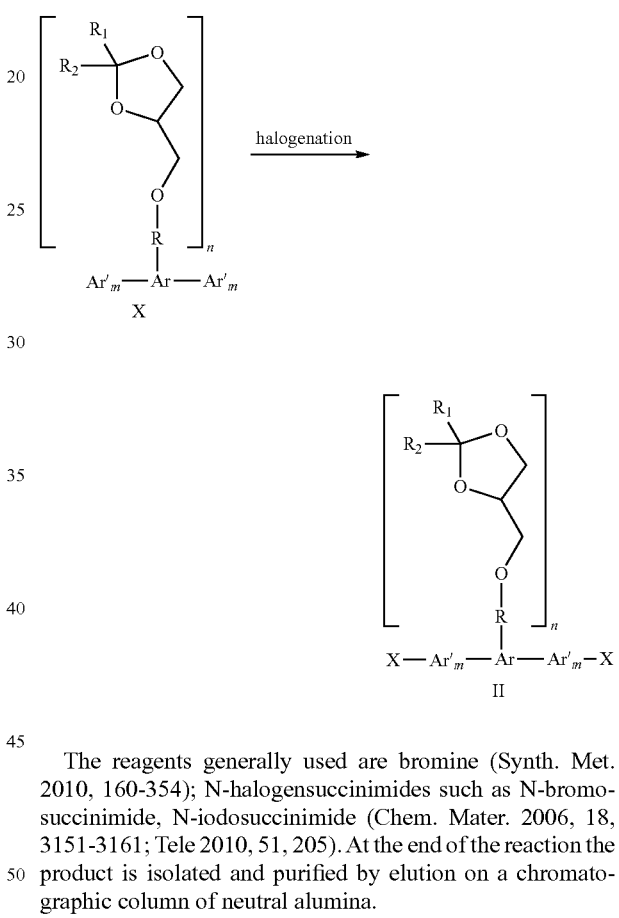

The reagents generally used are bromine (Synth. Met. 2010, 160-354); N-halogensuccinimides such as N-bromosuccinimide, N-iodosuccinimide (Chem. Mater. 2006, 18, 3151-3161; Tele 2010, 51, 205). At the end of the reaction the product is isolated and purified by elution on a chromatographic column of neutral alumina.

The process for obtaining the conjugated water-soluble polymer/copolymer, object of the present invention, provides for the reaction of at least one compound (I) or (II) with one or more co-monomers selected from those described hereunder:

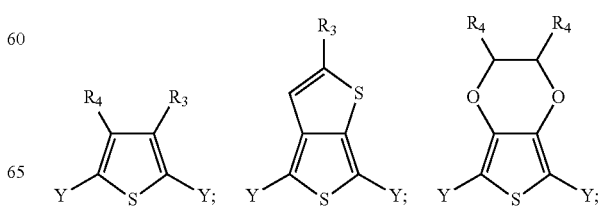

-continued
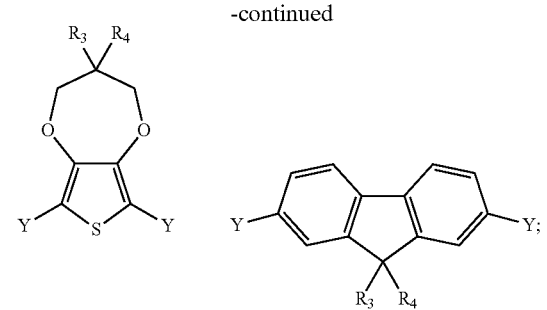
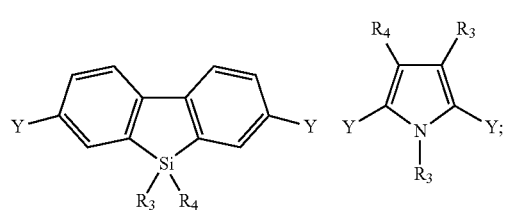
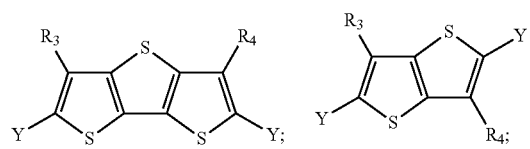
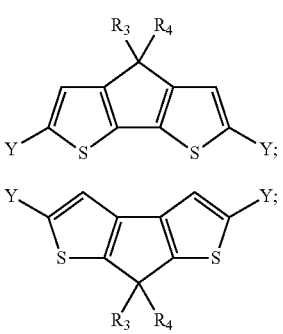
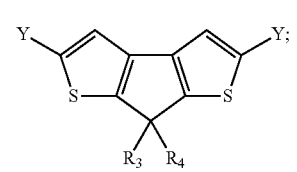
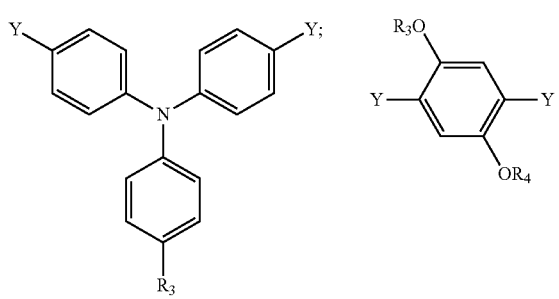
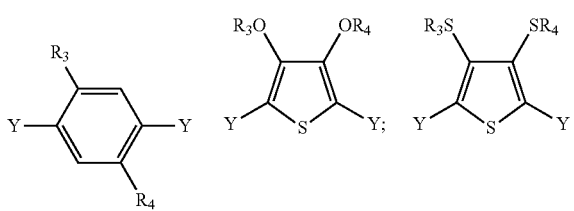
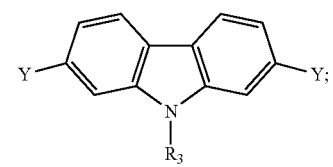
-continued
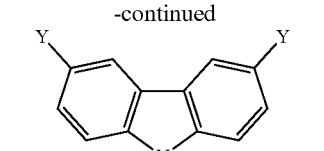
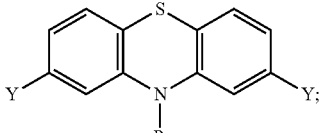
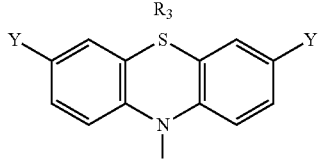
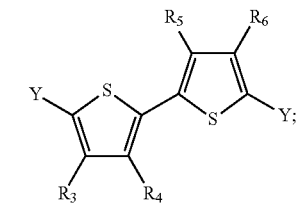
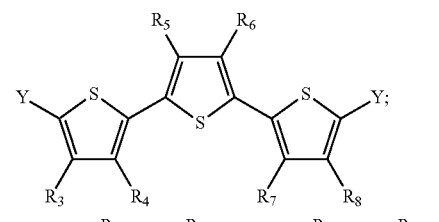
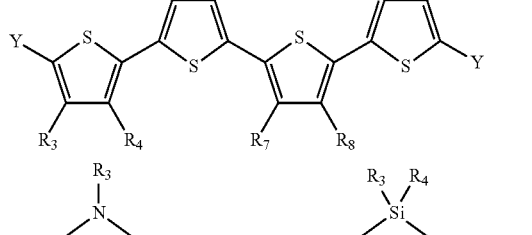
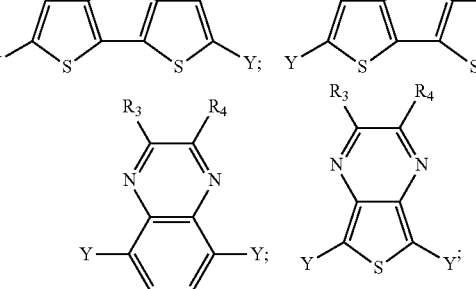
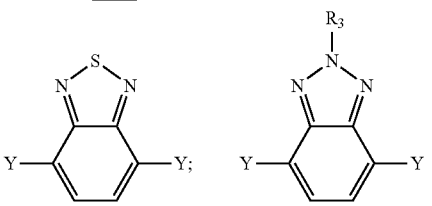

wherein
- $R_3$-$R_{10}$, equal or different from each other, are hydrogen atoms; $C_1$-$C_{37}$ alkyls, possibly branched, such as, for example, methyl, ethyl, propyl, butyl, hexyl, octyl, decyl, dodecyl, tetradecyl, hexadecyl, octadecyl, eicosyl, 2-ethylhexyl, 2-ethyloctyl, 2-ethyldecyl, 2-ethyldodecyl, 4-butylhexyl, 4-butyloctyl, 4-butyldecyl, 4-butyldodecyl, 2-hexyloctyl, 2-hexyldecyl, 4-hexyldecyl, isopropyl, 1-ethylpropyl, 1-butylpentyl, 1-hexylheptyl, 1-octylnonyl, 1-dodecyltridecyl, 1-hexadecylheptadecyl, 1-octadecylnonadecyl; if the radical is linked to a carbon atom, $R_3$-$R_{10}$ can be —$OC_1$—$OC_{16}$ alkoxyl groups.
- Y is a polymerizable group by means of a reaction selected from those of Suzuki, Stille, Heck or Yamamoto, selected from —Br, —Cl, —I, —O—($SO_2$)—$CF_3$, —B(oH)$_2$, —B(OR')$_2$, —SnR'$_3$, —B(OR"O), vinyl, with R' $C_1$-$C_6$ alkyl radical and R" ethylene radical, possibly substituted with $C_1$-$C_2$ alkyl groups.

The polymerization reaction takes place by resorting to a condensation reaction catalyzed by a derivative of a transition metal, which could be Palladium, in the case of Suzuki, Stille and Heck reactions, or Nickel in the case of a Yamamoto reaction.

Suzuki, Stille, Heck and Yamamoto reactions are known by experts in the field and are described in Chem. Rev., 1995, 95, 2457; J. Am. Chem. Soc., 1995, 117, 12426; J. Poly. Sci., Polym. Lett. Ed., 1980. 18, 9; Makromol. Chem., 1988, 189, 119.

The Suzuki polymerization provides, in its most general form, the reaction between a monomer having boron functionalities (acid or ester) with a monomer carrying halogens, such as bromine or iodine, or a trifluoromethanesulfonate group. The reaction can be carried out in a homogeneous solution (with a solvent selected, for example, from tetrahydrofuran, dioxane, dimethylformamide, toluene, etc.) or in mixtures of an organic solvent with water. In this second case, a phase-transfer agent, such as a tetra-alkylammonium salt, is generally used.

The reaction takes place in the presence of bases, such as sodium carbonate, sodium bicarbonate, tetra-alkylammonium hydroxides, caesium fluoride and is catalyzed by coordination complexes of palladium, such as palladium tetrakis (triphenylphosphine) or palladium tetrakis(o-tolylphosphine), which can possibly also be obtained in situ starting from a palladium salt such as palladium acetate or palladium chloride and a phosphine.

The Stille polymerization provides, in its most general form, the reaction between a monomer having trialkylstannyl functionalities with a monomer carrying halogens such as bromine or iodine. The reaction is carried out in a homogeneous solution (tetrahydrofuran, dioxane, dimethylformamide, toluene). The reaction is catalyzed by coordination complexes of palladium, such as palladium tetrakis(triphenylphosphine) or palladium tetrakis(o-tolylphosphine), which can possibly also be obtained in situ starting from a palladium salt such as palladium acetate or palladium chloride and a phosphine The Yamamoto polymerization provides, in its most general form, the reaction of a monomer carrying halogens such as bromine or iodine. The reaction is carried out in an organic solvent and is catalyzed by coordination complexes of nickel, for example cyclooctadienyl nickel.

The Heck polymerization provides, in its most general form, the reaction between a monomer having vinyl functionalities with a monomer carrying halogens such as bromine or iodine. The reaction is carried out in an organic solvent and is catalyzed by coordination complexes of palladium, such as palladium tetrakis(tri-phenylphosphine) or palladium tetrakis(o-tolylphosphine), which can possibly also be obtained in situ starting from a palladium salt such as palladium acetate or palladium chloride and a phosphine.

Once the copolymer has been obtained, and after isolating it using methods known to experts in the field, the resulting product is treated under acid hydrolysis conditions, for example in the presence of alcohols such as methanol, ethanol, butanol, etc; or ketones, such as acetone, and water or mixtures of these solvents. The reaction is carried out in an acid environment by hydrochloric acid or p-toluenesulfonic acid, generally HCl, to transform the dioxolane groups present along the chain into the corresponding diol groups:

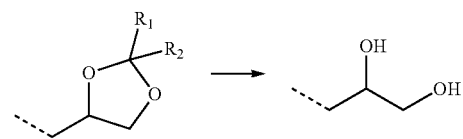

The hydrolysis of ketals/acetals is part of the known art of organic synthesis (Protective Groups in Organic Synthesis—T. W. Greene 1981, page 73.

The final copolymer proves to be soluble in water, alcohols or water/alcohol, water/acetone, water/THF mixtures and can be used, in combination with an acceptor compound soluble in the same solvent, for example a functionalized fullerene, for the formation of thin layers for solar cells.

Some illustrative and non-limiting examples are provided for a better understanding of the present invention and for its practical embodiment.

Example 1

Synthesis of 2,7-dibromo-9,9-bis(3'-bromopropyl)fluorene (Intermediate)

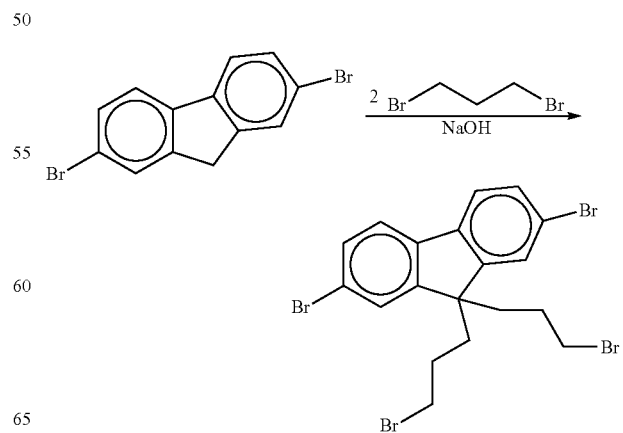

The following products are added, in an inert atmosphere, to a solution of 2,7-dibromofluorene (10.0 g, 31.06 mmoles) in 40 ml of 1,3-dibromopropane: first sodium hydroxide (30.0 g, 750.0 mmoles) dissolved in 60 ml of water and finally 0.2 g of tetrabutylammonium bromide. The temperature is brought to 100° C. After 6 hours, after the addition of water, extraction is effected with dichloromethane. After washing the organic phase with water until neutrality, said organic phase is anhydrified on sodium sulfate. The dichloromethane and 1,3-dibromopropane in excess are removed by distillation at reduced pressure. After purification by elution on a chromatographic silica gel column (eluent: heptane/ethyl acetate=99/1), 5.2 g of 2,7-dibromo-9,9-bis(3'-bromopropyl) fluorene are obtained (yield=30%).

Synthesis of 2,7-dibromo-9,9-bis{3-[(2,2-dimethyl-1,3-dioxolan-4-yl)methoxy]propyl}fluorene

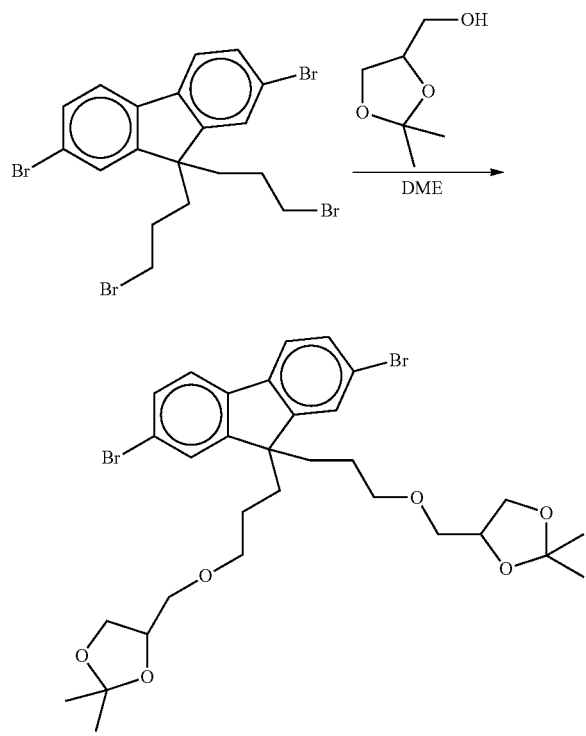

Potassium terbutylate (3.0 g, 26.7 mmoles) are added, in an inert atmosphere, to a solution of solketal (3.5 g, 26.7 mmoles) in 50.0 ml of 1,2-dimethoxyethane. After 20 minutes, 5.0 g of 2,7-dibromo-9,9-bis(3'-bromopropyl)fluorene (5.0 g, 8.9 mmoles) dissolved in 15.0 ml of 1,2-dimethoxyethane are added.

After 8 hours, after removing 1,2-dimethoxyethane by distillation at reduced pressure, the residue is recovered with ethyl acetate and is washed with water until neutrality. After anhydrifying the organic phase on sodium sulfate, the solvent is removed by distillation at reduced pressure. After purification by elution on a chromatographic alumina column (heptane/ethyl acetate=95/5), 4.0 g of 2,7-dibromo-9,9-bis{3-[(2,2-dimethyl-1,3-dioxolan-4-yl)methoxy]propyl}fluorene are obtained (yield=74%).

Example 2

Synthesis of 2,5-dibromo-3-methylthiophene (First Intermediate)

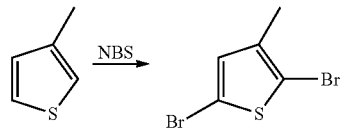

N-bromosuccinimide (20.0 g, 113.0 mmoles) is added, in an inert atmosphere to 3-methylthiophene (5.0 g, 51.0 mmoles) dissolved in 40 ml of tetrahydrofuran and 40 ml of acetic acid. After 1 hour, water is added and extraction is effected with ethyl ether.

After washing the organic phase to neutrality, first with water and then with a saturated aqueous solution of sodium bicarbonate, said organic phase is anhydrified on sodium sulfate. The solvent is distilled at reduced pressure. 9.7 g of 2,5-dibromo-3-methylthiophene are obtained (yield=75%)

Synthesis of 2,5-dibromo-3-bromomethylthiophene (Second Intermediate)

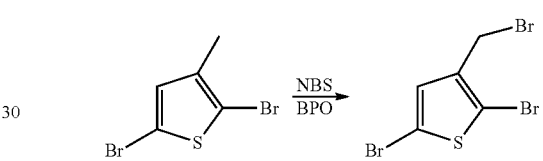

The following products are added, in an inert atmosphere to a solution of 2,5-dibromo-3-bromomethylthiophene (5.6 g, 22.0 mmoles) in 50 ml of carbon tetrachloride: N-bromosuccinimide (4.4 g, 24.9 mmoles) and finally 50 mg of dibenzoylperoxide. After 7 hours, water is added and extraction is effected with ethyl acetate. After washing the organic phase to neutrality with water, said organic phase is anhydrified on sodium sulfate. After removing the solvent by distillation at reduced pressure, 5.0 g of 2,5-dimethyl-3-bromomethylthiophene are obtained (yield=70%).

Synthesis of 4-{[(2,5-dibromo-3-thienyl)methoxy]methyl}-2,2-dimethyl-1,3-dioxolane

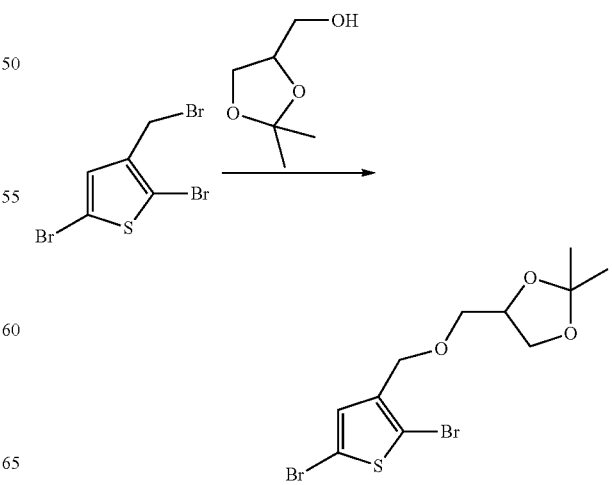

Potassium terbutylate (2.6 g, 23.2 mmoles) are added, in an inert atmosphere, to a solution of solketal (3.1 g, 23.5 mmoles) in 35.5 ml of 1,2-dimethoxyethane. After 15 minutes, 2,5-dimethyl-3-bromomethylthiophene (5.0 g, 15.0 mmoles) dissolved in 15 ml of 1,2-dimethoxyethane, are added dropwise.

After 3 hours, the 1,2-dimethoxyethane is removed by distillation at reduced pressure, the residue is recovered with water and extracted with ethyl acetate. After washing the organic phase with water until neutrality, said organic phase is anhydrified on sodium sulfate. The solvent is removed by distillation at reduced pressure. After purification by elution on an alumina column (heptane/ethyl acetate=95/5), 4.0 g of 4-{[(2,5-dibromo-3-thienyl)methoxy]methyl}-2,2-dimethyl-1,3-dioxolane are obtained (yield=70%).

Example 3

Synthesis of 3,6-dibromo-9-(3'-bromopropyl)carbazole (Intermediate)

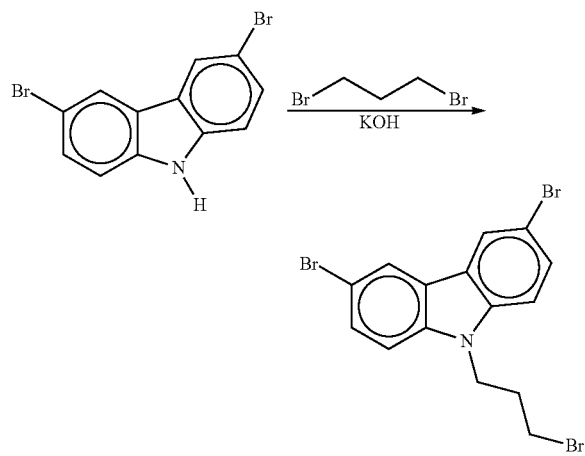

The following products are added, in an inert atmosphere, to a solution of 3,6-dibromocarbazole (2.5 g, 7.74 mmoles) in 13 ml of toluene: potassium hydroxide (6.5 g, 98 mmoles) dissolved in 13 ml of water, tetrabutylammonium bromide and finally 1,3-dibromopropane (9.9 g, 49.2 mmoles).

The temperature is brought to 70° C. After 3 hours, water is added and extraction is effected with ethyl acetate. After washing the organic phase with water to neutrality, said organic phase is anhydrified on sodium sulfate. After removing the solvent by distillation at reduced pressure 2.5 g of 3,6-dibromo-9-(3'-bromopropyl)carbazole are obtained (yield=75%).

Synthesis of 3,6-dibromo-9-{3-[(2,2-dimethyl-1,3-di-oxolan-4-yl)methoxy]propyl}-9H-carbazole

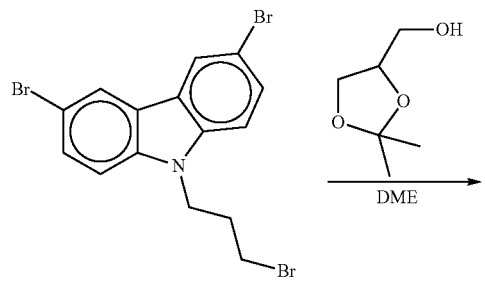

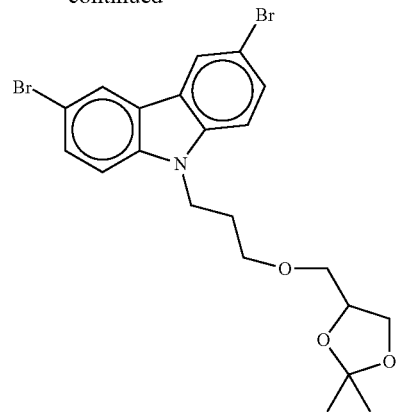

Potassium terbutylate (0.8 g, 7.1 mmoles) are added, in an inert atmosphere, to a solution of solketal (0.9 g, 7.1 mmoles) in 10 ml of 1,2-dimethoxyethane. After 15 minutes, 3,6-dibromo-9-(3'-bromopropyl)carbazole (2.1 g, 4.7 mmoles) dissolved in 10 ml of 1,2-dimethoxyethane, are added dropwise. After hours, the 1,2-dimethoxyethane is removed by distillation at reduced pressure, the residue is recovered with water and extracted with ethyl acetate. After washing the organic phase with water until neutrality, said organic phase is anhydrified on sodium sulfate. The solvent is removed by distillation at reduced pressure. After purification by elution on an alumina column (heptane/ethyl acetate=9/1), 1.6 g of 3,6-dibromo-9-{(3-[(2,2-dimethyl-1,3-di-oxolan-4-yl)methoxy]propyl}-9H-carbazole are obtained (yield=70%).

Example 4

Synthesis of the random copolymer poly{(2,1,3-benzothiadiazole)-alt-[(3-(4-sodiumsulfobutoxy)methylthiophene)-co-(9,9-bis-(3-((2,2-dimethyl-1,3-dioxolan-4-yl)methoxy)propyl)fluorene)]}

The following products are introduced in an inert atmosphere into a 50 ml two-necked flask equipped with a magnetic stirrer and reflux cooler:
  324.3 mg (0.485 mmoles) of 2,7-dibromo-9,9-bis{3-[(2,2-dimethyl-1,3-dioxolan-4-yl)methoxy]propyl}fluorene;
  373.80 mg (0.963 mmoles) of 4,7-bis(pinacolboronic-2,1,3-benzothiadiazole) ester;
  200.6 mg (0.482 mmoles) of [(2,5-dibromo-3-thienyl)methoxy]sodium butanesulfonate;
  10 ml of distilled THF (tetrahydrofuran);
  1 ml of an aqueous solution 4 M of $K_2CO_3$;
  a few drops of Aliquat 334.

The reaction mixture is heated to 70° C. for 15 minutes and the following product is then added:
  12 mg (0,01 mmoles) of Pd (0) tetrakis(triphenylphosphine);

The reaction mixture is left at this temperature for 40 hours. After 5 hours the reaction is almost dry and a further 5 ml of THF are added. After 40 hours the mixture is cooled and the solvent removed by distillation.

Hydrolysis of poly{(2,1,3-benzothiadiazole)-alt-[(3-(4-sodiumsulfobutoxy)methylthiophene)-co-(9,9-bis-(3-((2,2-dimethyl-1,3-dioxolan-4-yl)methoxy)propyl)fluorene)]}

The following products are introduced into a 250 ml two-necked flask:

600 mg of random copolymer between 2,7-dibromo-9,9-bis{3-[(2,2-dimethyl-1,3-dioxolan-4-yl)methoxy]propyl}-fluorene, 4,7-bis pinacolboronic-2,1,3-benzothiadiazole ester and [(2,5-dibromo-3-thienyl)methoxy] sodium butanesulfonate, previously prepared, 45 ml of acetone;

35 ml of water;

5 ml of HCl at 37%.

After 18 hours, the mixture is cooled to room temperature. The solution is at neutral pH, as resulting from a litmus paper test. The solvent is then removed by distillation. The polymer is re-dissolved in a solution consisting of 45 ml of acetone and 5 ml of distilled water.

The solution containing the polymer is transferred to a dialysis membrane with a cut-off at 1,200 Da and dialyzed for 2 days in a 1l cylinder also containing an acetone/water solution in a weight ratio of 9:1.

The solvent is removed from the solution containing the polymer by distillation. 375 mg of a dark red polymer are obtained.

The NMR spectrum shows the disappearance of the signals due to the methyl groups of the dioxolane groups and their transformation into glycol groups.

The invention claim is:

1. A monomer of formula (I):

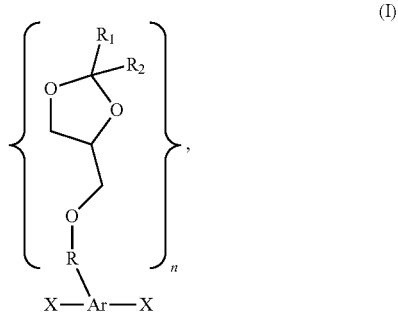

wherein:

Ar represents a $C_6$-$C_{12}$ aromatic radical, a $C_{12}$-$C_{18}$ polycyclic aromatic radical, or a heteroaromatic radical comprising a heteroatom, optionally polycondensed;

X represents a functional group which can be polymerized by Suzuki, Stille, Heck or Yamamoto reaction, said functional group selected from the group consisting of —Br, —Cl, —I, —O—($SO_2$)—$CF_3$, —B(OH)$_2$, —B(OR')$_2$, —SnR'$_3$, —B(OR"O) and vinyl, such that R' represents a $C_1$-$C_6$ alkyl radical and R" represents an ethylene radical, optionally substituted with $C_1$-$C_2$ alkyl groups;

$R_1$ and $R_2$ independently represent a hydrogen atom or a $C_1$-$C_6$ alkyl radical;

R represents a divalent $C_1$ or $C_3$ alkylene radical; and n ranges from 1 to 4.

2. The monomer of claim 1, wherein Ar is a radical obtained from benzene, fluorene, thiophene, carbazole, dithienocyclopentadiene or from phenothiazine.

3. A process for synthesizing the monomer of claim 1, the process comprising reacting by etherification a halogen-derivative of formula (III) with the hydroxyl group of a glycerol of formula (IV):

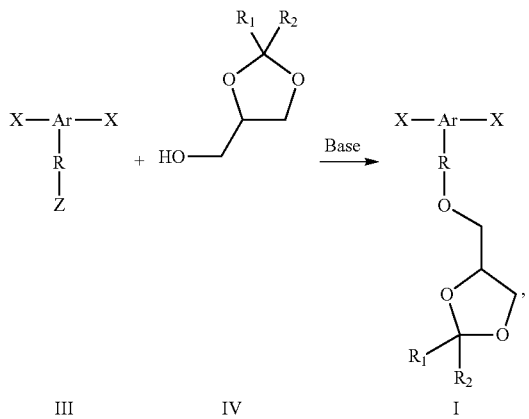

to form the monomer of formula (I), wherein Z=Cl, Br or I.

4. The process according to claim 3, wherein a molar ratio of an amount of the halogen-derivative of formula (III) : to an amount of the glycerol of formula (IV) : to an amount of a base present in the etherification ranges from 1:1.1:1.15 to 1:3:3.3.

5. The process according to claim 3, wherein the etherification occurs at temperatures ranging from 15° C. to 150° C.

6. A process for preparing a conjugated polymer or copolymer, the process comprising reacting at least one monomer of claim 1 with at least one co-monomer selected from the group consisting of:

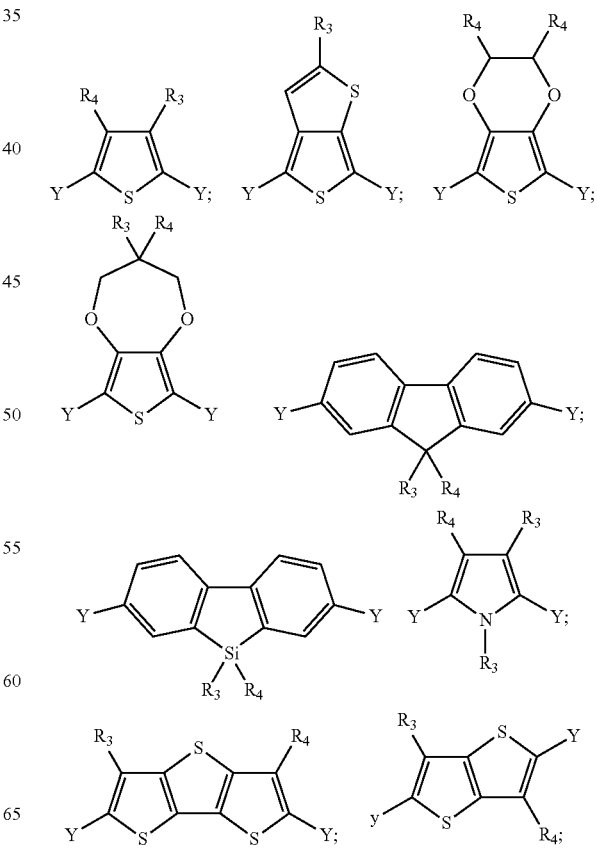

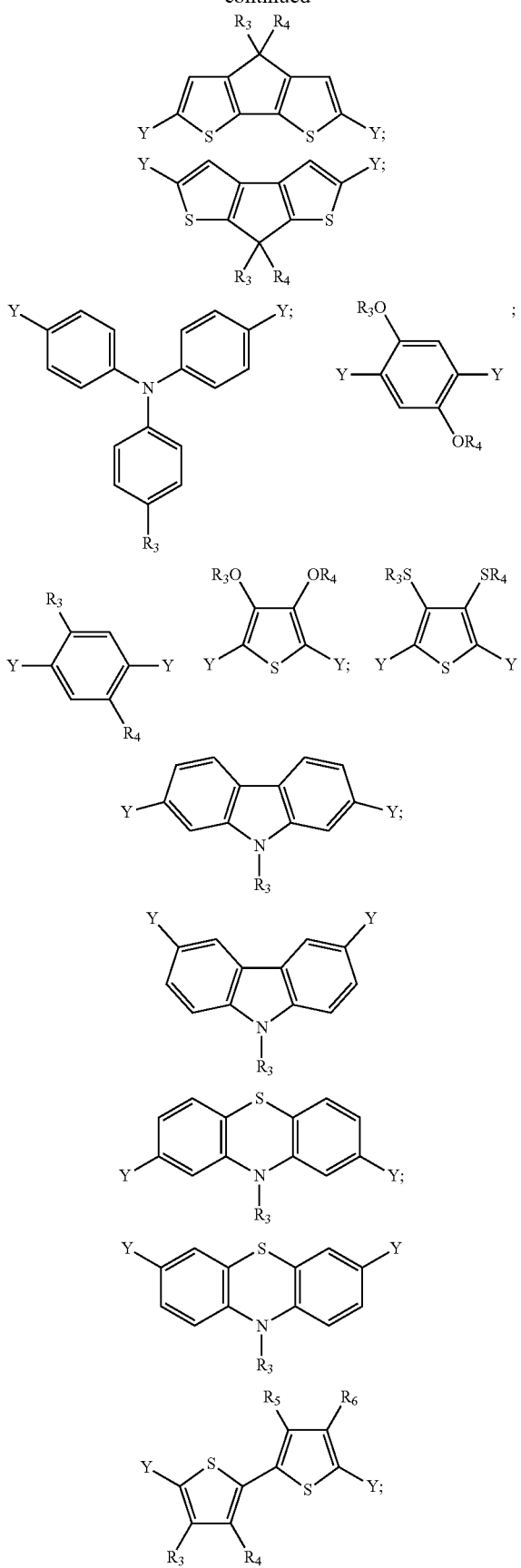
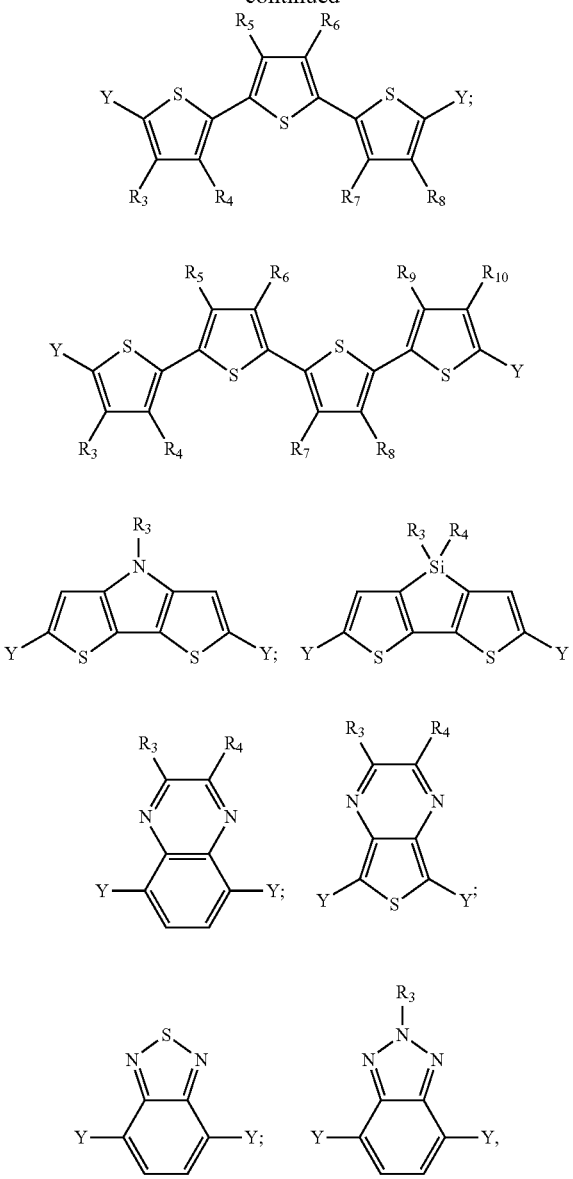

followed by acid hydrolysis of an initially-obtained polymer or copolymer, to yield a conjugated polymer or copolymer, wherein:

$R_3$-$R_{10}$ independently represents a hydrogen atom, an optionally branched $C_1$-$C_{37}$ alkyl group, and an —$OC_1$—$OC_{16}$ alkoxyl group; and Y is a group which can be polymerized by Suzuki, Stille, Heck or Yamamoto reaction.

7. The process according to claim 6, wherein the reacting occurs by a condensation reaction, which is catalyzed by a derivative of:

palladium, in the case of a Suzuki, Stille or Heck reaction or nickel, in the case of a Yamamoto reaction.

8. The process according to claim 4, wherein the etherification occurs at temperatures ranging from 15° C. to 150° C.

9. The process of claim 6, wherein the polymer or copolymer is soluble in water.

10. A monomer of formula (I):

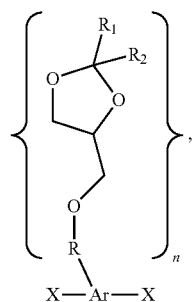

wherein:
Ar represents a $C_6$-$C_{12}$ aromatic radical, a $C_{12}$-$C_{18}$ polycyclic aromatic radical, or a heteroaromatic radical comprising a heteroatom, optionally polycondensed;

X represents a functional group which can be polymerized by Suzuki, Stille, Heck or Yamamoto reaction, said functional group selected from the group consisting of —Br, —Cl, —I, —O—($SO_2$)—$CF_3$, —B(OH)$_2$, —B(OR')$_2$, —SnR'$_3$, —B(OR"O) and vinyl, such that R' represents a $C_1$-$C_6$ alkyl radical and R" represents an ethylene radical, optionally substituted with $C_1$-$C_2$ alkyl groups;

$R_1$ and $R_2$ independently represent a hydrogen atom or a $C_1$-$C_6$ alkyl radical;

R represents a divalent $C_3$-$C_{12}$ alkylene radical; and n ranges from 1 to 4.

11. The monomer of claim 1, wherein Ar represents a $C_{12}$-$C_{18}$ polycyclic aromatic radical, or a heteroaromatic radical comprising a heteroatom, optionally polycondensed.

* * * * *